(12) United States Patent
Chang et al.

(10) Patent No.: US 6,939,978 B2
(45) Date of Patent: Sep. 6, 2005

(54) PRODUCTION OF TAXOL AND TAXANES

(75) Inventors: Ching-jer Chang, Lafayette, IN (US); Xiao-jie Tong, Palisades Park, NJ (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 10/193,664

(22) Filed: Jul. 10, 2002

(65) Prior Publication Data

US 2003/0013899 A1 Jan. 16, 2003

Related U.S. Application Data

(63) Continuation of application No. PCT/US01/00786, filed on Jan. 10, 2001.
(60) Provisional application No. 60/175,837, filed on Jan. 13, 2000.

(51) Int. Cl.$^7$ ............................................. C07D 305/14
(52) U.S. Cl. ...................... 549/510; 549/511; 435/123
(58) Field of Search ................................ 549/510, 511; 435/123

(56) References Cited

U.S. PATENT DOCUMENTS

| | | | |
|---|---|---|---|
| 3,418,262 A | 12/1968 | Wérotte et al. | ................ 521/32 |
| 5,279,949 A | 1/1994 | Nair | ........................... 435/123 |
| 5,281,727 A | * 1/1994 | Carver et al. | ................ 549/510 |
| 5,475,120 A | * 12/1995 | Rao | ............................ 549/510 |
| 5,654,448 A | 8/1997 | Pandey et al. | ............... 549/510 |
| 5,744,333 A | 4/1998 | Cociancich et al. | ........ 435/123 |
| 5,969,165 A | 10/1999 | Liu | ............................. 549/510 |

FOREIGN PATENT DOCUMENTS

| | | |
|---|---|---|
| WO | 92/07842 | 5/1992 |
| WO | 92/18492 | 10/1992 |
| WO | 94/13827 | 6/1994 |
| WO | 98/07712 | 2/1998 |

OTHER PUBLICATIONS

Goldspiel, B.R. (1997) "Clinical Overview of the Taxanes" *Phamacotherapy*, 17(5):110S–125S.

Kingston, D.G.I. (1995) "Natural Taxoids: Structure and Chemistry" *Taxol: Science and Applications*, M. Suffness, ed., CRC Press, Inc., Boca Raton, Florida, pp. 287–315.

Miller, R.W. et al. (1981) "Antileukemic Alkaloids from *Taxus wallichiana* Zucc." *J. Org. Chem.*, 46:1469–1474.

Snader, K.M. (1995) "Isolation and Detection" *Taxol– Science and Applications*, M. Suffness, ed., CRC Press, Inc., Boca Raton, Florida, pp. 277–286.

Wani, M.C. et al. (1971) "Plant Antitumor Agents. VI. The Isolation and Structure of Taxol a Novel Antileukemic and Antitumor Agent from *Taxus brevifolia*" *J. Am. Chem. Soc.*, 93(9):2325–2327.

Witherup, K. et al. (1990), "*Taxus* Spp. Needles Contain Amounts of Taxol Comparable to the Bark of *Taxus Brevifolia*: Analysis and Isolation" *J. Nat. Prod.* 53(5):1249–1255.

* cited by examiner

Primary Examiner—Ba K. Trinh
(74) Attorney, Agent, or Firm—Greenlee, Winner and Sullivan, P.C.

(57) ABSTRACT

A high yield, economical process for purifying taxanes from yew biomass is disclosed. The process does not require initial liquid:liquid portioning of the crude extract to separate highly polar substances. The organic solvent extract of the biomass is adsorbed onto and selectively desorbed from an adsorption resin to provide a taxane enriched eluate. Substantially pure individual taxanes may be further isolated from the eluate by hydrophobic-interaction chromatography.

35 Claims, 6 Drawing Sheets

| Peak # | RetTime [min] | Type | Width [min] | Area [mAU*s] | Height [mAU] | Area % | |
|---|---|---|---|---|---|---|---|
| 1 | 5.235 | PV | 0.1239 | 2.86622 | 3.48750e-1 | 0.0119 | |
| 2 | 5.408 | VB | 0.1748 | 3.87487 | 3.16651e-1 | 0.0161 | |
| 3 | 6.064 | BB | 0.1503 | 7.74179 | 7.90413e-1 | 0.0322 | |
| 4 | 8.905 | BP | 0.2280 | 3.50630 | 2.37768e-1 | 0.0146 | |
| 5 | 17.681 | PP | 0.3308 | 7.29730 | 3.14345e-1 | 0.0304 | |
| 6 | 19.066 | BP | 0.4515 | 13.86482 | 3.74879e-1 | 0.0577 | |
| 7 | 23.825 | BB | 0.4093 | 12.59547 | 4.51765e-1 | 0.0524 | |
| 8 | 26.091 | PV | 0.6041 | 91.92912 | 2.35164 | 0.3825 | |
| 9 | 27.095 | VP | 0.5899 | 36.53817 | 8.84512e-1 | 0.1520 | |
| 10 | 29.424 | PP | 0.8866 | 49.18968 | 7.22218e-1 | 0.2046 | |
| 11 | 32.496 | VB | 0.7287 | 2.36516e4 | 502.90894 | 98.3983 | Taxol |
| 12 | 35.434 | BB | 0.7655 | 40.95779 | 7.49535e-1 | 0.1704 | |
| 13 | 37.651 | PB | 0.7513 | 24.14595 | 4.24730e-1 | 0.1005 | |
| 14 | 40.290 | BP | 0.5071 | 39.12063 | 1.13212 | 0.1628 | |
| 15 | 41.994 | VP | 0.4428 | 42.65605 | 1.43498 | 0.1775 | |
| 16 | 46.239 | PB | 0.2940 | 8.70085 | 4.57262e-1 | 0.0362 | |

PRODUCTION OF TAXOL AND TAXANES

CROSS REFERENCE TO RELATED APPLICATION

This application is a continuation of International Application number PCT/US01/00786 filed on Jan. 10, 2001, which claims the benefit of U.S. Provisional Application Ser. No. 60/175,837 filed on Jan. 13, 2000, both of which are hereby incorporated by reference to the extent not inconsistent with the disclosure herewith.

STATEMENT REGARDING FEDERAL RESEARCH SUPPORT

This application was supported, at least in part, with funding from the National Institute of Health, Contract No. CA55118 and CA49632. Accordingly, the U.S. government may have certain rights in this invention.

FIELD OF THE INVENTION

This invention relates to a process to purify taxanes from plant biomass. More specifically, this invention relates to a high yield extraction and purification process to obtain taxol and taxanes from yew biomass.

BACKGROUND OF THE INVENTION

Taxol is a naturally occurring compound originally isolated from the stem bark of the Western Yew, *Taxus brevifolia* (Wani et al., J. Am. Chem. Soc., vol. 93 (1971), pg. 2325). Taxol is an important chemotherapeutic agent for the treatment of human ovarian, breast and lung cancers and is considered as a promising therapeutic agent for the treatment of other human cancers (Goldspiel, "Clinical Overview of the Taxanes", Pharmacotherapy, vol. 17 (1997), pg. 110S and McGuire and Rowinsky, "Paclitaxel in Cancer Treatment", Marcel Dekker, Inc., New York, 1995). Taxanes such as taxol, cephalomannine, baccatin III, and their 10-deacylated and 7-xylosyl derivatives are characterized by a highly complicated diterpene skeleton. These chemically similar compounds are frequently found together in complex extracts of different parts of yews. The isolation of individual taxanes from such extracts generally requires reverse phase chromatographic methods using expensive reverse phase silica based gel matrices, or alternatively, using silica gel or alumina matrices with very slow gradient elution systems (Snader, "Isolation and Detection," in *Taxol-Science and Applications*, M. Suffness, ed., CRC Press, Boca Raton, Fla. 1995, pp. 277–286). Low isolation yields of desired compounds, the high costs of the chromatographic resins and/or regeneration of these resins are often unsatisfactory and contribute to high production costs.

The first isolation of taxol used a methanol extract from the bark of *T. brevifolia* followed by a series of chromatographic steps using FLORISIL®, SEPHADEX LH-20® and silica gel (Wani et al., J. Am. Chem. Soc., vol. 93 (1971), pg. 2325). Miller et al., J. Org. Chem., vol. 46 (1981), pg. 1469, describes the isolation of taxol and cephalomannine by ethanol extraction of the needles, twigs and roots of yews followed by counter current distribution, reverse phase chromatography and silica gel chromatography.

Production of taxol and other taxanes from yew biomass by prior art methods has been hindered by the often high levels of impurities in initial extracts. Various fractionation and filtration procedures have been used to enrich extracts before further purification. These include methods described in Rao WO 92/07842; Nair WO 94/13827; Elsohley et al. WO 92/18492; Carver et al. U.S. Pat. No. 5,281,727, issued Jan. 25, 1994; Pandey and Yankov, U.S. Pat. No. 5,654,448, issued Aug. 5, 1987; Cociancich and Pace, U.S. Pat. No. 5,744,333, issued Apr. 28, 1998; Liu U.S. Pat. No. 5,969, 165, issued Oct. 19, 1999; and Snader, "Isolation and Detection," in *Taxol-Science and Applications*, M. Suffness, ed., CRC Press, Boca Raton, Fla. 1995, pp. 277–286. Features shared by all these methods are an initial organic solvent extraction of the biomass, followed by one or more liquid:liquid partitioning steps to remove impurities, followed in turn by multiple chromatographic purification steps. Due to the low content of taxol in yew biomass (0.05–0.001% of dry weight), extraordinarily large amounts of organic solvents such as chloroform, methylene chloride and benzene are used in the extraction and partitioning procedures. These solvents are generally toxic and require costly emission control and waste management systems. In addition, the partitioning steps are highly prone to the formation of emulsions that seriously jeopardize the partition efficiency.

Nair, in WO 94/13827 and Liu in U.S. Pat. No. 5,969,165 disclose that treatment of a crude extract with activated charcoal as an essential step to avoid problems in downstream chromatographic separation steps. After removing the charcoal, the resulting clarified solution was fractionated either by precipitating the taxanes or by liquid:liquid partitioning steps to remove water soluble impurities prior to chromatography. Activated charcoal can absorb substantial amounts of the desired taxanes along with the impurities, and the liquid:liquid partitioning step can involve toxic solvents. This significantly reduces the process yield and can increase costs to isolate individual taxane compounds.

All of these drawbacks make the production of taxol and other taxanes from needles and twigs economically less attractive than the wholesale extraction from bark where the concentration of taxol is high and the concentration of problematic impurities tends to be relatively lower. However, there is concern that the isolation of taxol from yew bark will not be able to provide sufficient quantities for all cancer patients and would endanger the survival of natural yew. It is therefore desirable to develop high yield methods of purification of taxol and other taxanes from renewable sources of natural or cultivated yew biomass (Witherup et al., J. Nat. Prod., vol. 53 (1990), pg. 1249).

The present invention overcomes the above-mentioned drawbacks and provides additional benefits and advantages. Advantages include providing a process for the high yield extraction and purification of taxol and other taxanes from yew biomass. Other benefits include eliminating costly partitioning process, thus dramatically reducing the use of toxic organic solvents and expensive silica-based reverse phase chromatographic matrices.

SUMMARY OF THE INVENTION

The present invention relates to a process for purifying taxanes from plant biomass and the manufacture thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

The present invention provides for a high yield, economical method and process for purifying taxanes from yew biomass, particularly from renewable biomass such as needles, twigs and/or stems. The process comprises extracting a preferably ground yew biomass with an extraction solvent selected for high solubility of taxanes in the solvent, followed by an enrichment of the extract in taxanes by selective adsorption onto and elution from an adsorption resin.

In one form, a process for purifying taxanes is provided. The process comprises: obtaining a crude extract containing impure taxanes from the plant biomass; absorbing the impure taxanes on an absorption resin; washing the absorption resin with a wash solvent; and eluting taxanes from the absorption resin with a elution solvent less polar than the wash solvent. The extract is adsorbed onto a silica resin and non-polar impurities washed from the resin with a relatively non-polar wash solvent. Taxanes are then eluted by appropriate selection of the elution solvent. Individual taxanes are then isolated from this eluate in greater than 90% purity by chromatography on a non-ionic, hydrophobic-interaction macropolymer resin.

In another form, individual taxanes may be isolated from a taxane containing biomass in high purity. The process for isolating taxanes comprises: extracting a plant biomass containing taxanes with an extraction solvent to provide a crude extract containing impure taxanes; adsorbing the impure taxanes on an adsorption resin prior to fractionation of the taxanes from the crude extract; and eluting one or more taxanes from the adsorption resin with an elution solvent to provide a taxane enriched eluate.

In yet another form, a process for the isolation of taxanes from a plant biomass comprising: extracting the biomass with an extraction solvent able to dissolve taxanes to obtain an extract containing desired taxanes and hydrophilic and hydrophobic impurities; adsorbing the extract onto a first non-ionic, hydrophobic interaction, macropolymer resin with a polar, buffered or unbuffered aqueous:organic solvent adsorption mixture that induces the absorption of desired taxanes onto the first hydrophobic-interaction resin; washing the first hydrophobic-interaction resin with a buffered or unbuffered aqueous:organic solvent wash mixture to elute impurities more hydrophilic than the desired taxanes from the first hydrophobic-interaction resin while retaining desired taxanes adsorbed on said first hydrophobic-interaction resin; eluting desired taxanes from said first hydrophobic-interaction resin with a buffered or unbuffered aqueous:organic solvent elution mixture that is more hydrophobic than the wash mixture and that induces desorption of desired taxanes from the first hydrophobic-interaction resin while retaining impurities more hydrophobic than the desired taxanes, adsorbed on the first hydrophobic-interaction resin to obtain an eluate enriched in desired taxanes.

In still yet another form of the present invention, there is provided an initial aqueous extraction of the biomass, prior to the extraction of taxanes, to remove water soluble proteins, salts, sugars and pigments. This is particularly advantageous when a silica adsorption resin is used as compared to a non-ionic hydrophobic-interaction adsorption resin in the subsequent steps of the process.

In a preferred embodiment, the adsorption resin comprises a macropolymer or copolymer of one or more polymers selected from the group consisting of polyaromatic, polyacrylate, polymethacrylate, polystyrene, brominated polystyrene and mixtures thereof. These resins are advantageously rechargeable by cleaning with non-polar organic solvents followed by re-equilibration with a desired adsorption solvent.

In other preferred embodiments, the adsorption resin comprises a copolymer of styrene and divinyl benzene produced by suspension copolymerization in water and a water immiscible organic solvent.

It is an object of the present invention to provide a method of producing taxanes in high yield and purity. These and other objects and benefits of the present invention will be apparent from the following detailed description of the preferred embodiments.

DESCRIPTION OF THE PREFERRED EMBODIMENTS

Figure 1:
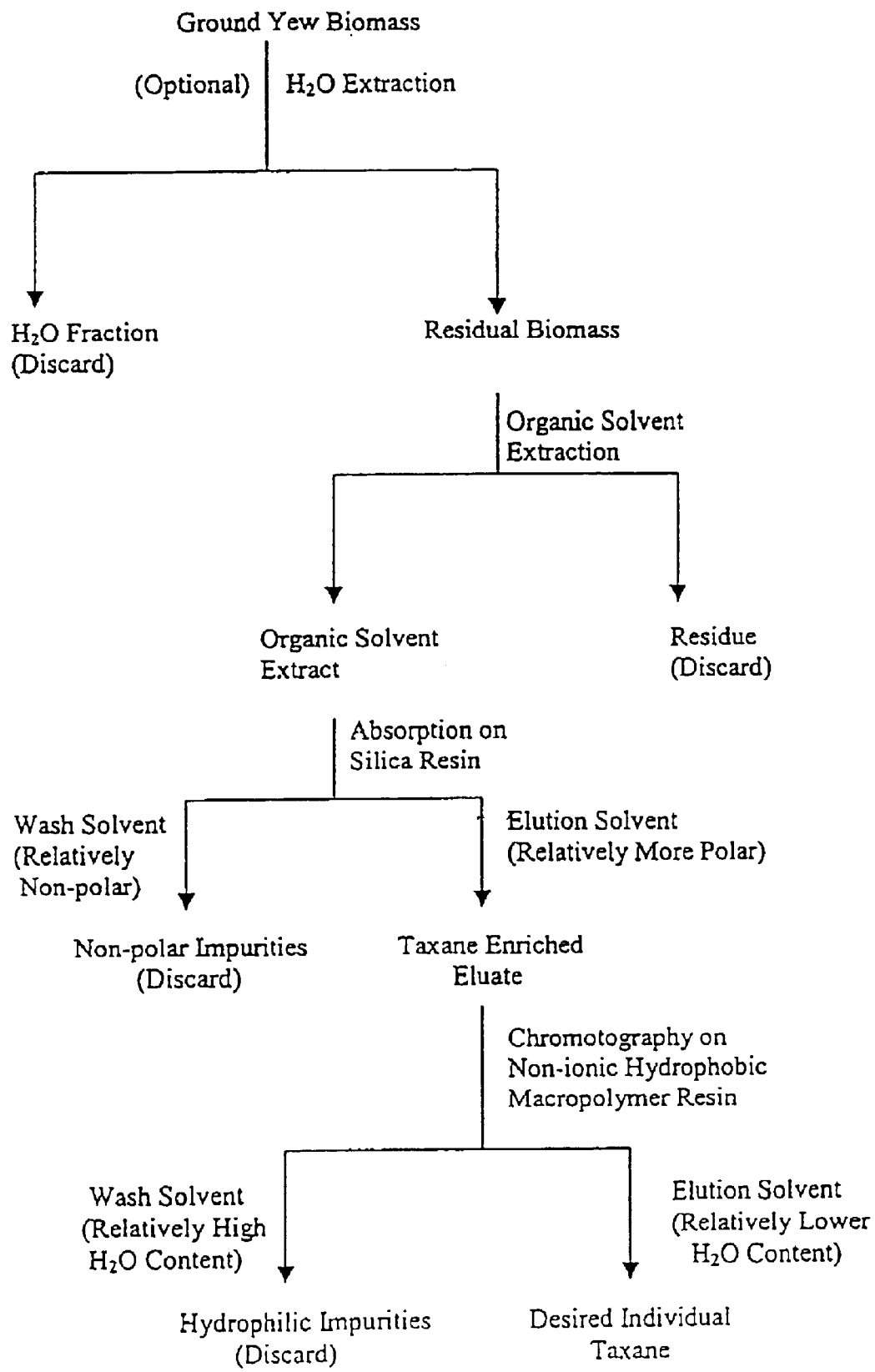
FIG. 1 is a process flow diagram illustrating one scheme for the isolation of taxanes from yew biomass according to this invention.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

The present invention provides an improved process for purifying taxanes from biomass derived from yews. The process provides for high yields of substantially pure taxanes and is more cost effective and environmentally friendly than prior art methods. Taxanes are first extracted with an organic extraction solvent from a ground biomass derived from yews. The taxanes are then adsorbed onto an adsorption resin. The resin is sequentially eluted with solvents of differing polarity to separate desired taxanes from impurities differing in polarity or hydrophobicity. Substantially pure individual taxanes are then isolated by chromatography on relatively inexpensive adsorption resins. For example, one purification scheme uses silica gel resin. Other purification schemes use a non-silica, hydrophobic-interaction macropolymer resin (a non-ionic resin) to isolate individual taxanes and remove residual impurities. Regardless of the purification scheme as described herein, this invention provides individual taxanes in high purity without the necessity of using highly toxic solvents, such as methylene chloride and chloroform.

Taxanes purified by the present invention include taxol, cephalomannine, baccatin III, 10-deacetyltaxol, 10-deacetylcephalomannine, 10-deacetylbaccatin III, 7-xylosyltaxol, 7-xylosylcephalomannine, 7-xylosylbaccatin III and like derivatives of taxol. These pharmaceutically important taxanes have been found in varying concentrations in many species of yew of the genera *Taxus* and *Austrotaxus,* including the Western Yew (Pacific Yew) and many other cultivated species derived from the hybridization of *T. buccata* and *T. cuspitata* due to their relatively high content of taxanes.

Valuable taxanes can be extracted from essentially any portion of yews and particularly from bark, needles, twigs, and roots. Yew bark extracts tend to have relatively higher concentrations of taxanes and relatively lower concentrations of problematic pigments, lipids, and waxes as compared to extracts from needles and twigs. However, stripping bark will permanently damage the trees. For this reason, it is preferred to extract taxanes from renewable biomass, as for example, needles and twigs or even plant cells in cultures.

Harvested yew biomass, whether from needles, twigs, roots, bark, or plant cells in cultures is preferably processed while fresh to minimize degradation of taxanes by natural processes. Freshly harvested biomass may be stored under cold, dry conditions for as long as one to several weeks with minimal reduction of taxane yield. However, it is usually not industrially practical to timely process fresh biomass. It is therefore preferable to dry the biomass after harvest if longer storage is desired. Methods for drying plant material are well known in the art and any number may by used in the present process, provided temperatures remain below about 40° C. to prevent the degradation and/or epimerization of taxanes, which can yield related analogs of taxanes. Dried biomass may be stored for long periods of time under dry conditions at or below room temperature. Rehydrating dried biomass prior to further processing can improve yields. Rehydration can be effected by immersing the biomass in water or other aqueous solution for a time selected from at least 10 minutes to several hours or longer.

Fresh, dried or rehydrated biomass can be shredded and ground by any conventional means known in the art. In a preferred embodiment, the biomass is ground to a particle size of less than or equal to ¼ inch (or 10 mesh).

In one embodiment of the present invention, before the ground biomass is extracted with the organic extraction solvent, it is first extracted with an aqueous solvent to remove water soluble proteins, salts, sugars and pigments that would otherwise contaminate the organic solvent extract.

In other embodiments of the present invention, ground biomass is extracted with an organic extraction solvent selected for high solubility of taxanes in the extraction solvent. Several suitable extraction solvents are known in the art. Preferred examples include $C_1$–$C_6$ alcohols, $C_3$–$C_7$ alkyl ketones, $C_1$–$C_4$ alkyl esters of $C_1$–$C_5$ carboxylic acids, $C_1$–$C_4$ carboxylic acids, $C_1$–$C_4$ alkyl nitiles, $C_4$–$C_8$ alkyl ethers, chloroform, methylene chloride, nitromethane, toluene and mixtures thereof. Water miscible solvents may further comprise up to about 60% water by volume. Methanol/methylene chloride mixtures provide a high extraction efficiency for taxanes from the biomass. However, the use of methylene chloride presents significantly increased material and waste disposal costs, as does the use of several other solvents listed above. Methanol provides excellent penetration into cells, solubility of taxanes, and low cost of materials and waste disposal. In addition, methanol is readily removed to concentrate the extract and/or yield a dry, crude taxane. Advantageously, methanol is readily recovered for recycling.

To extract the biomass, a selected organic extraction solvent is added to the biomass. The resulting mixture is allowed to soak for a desired period of time. The desired period of time can be the minimal time required to physically add the solvent and subsequently separate it from the residual solids. Preferably, the mixture is maintain with or without agitation for a time ranging from a few minutes to several hours, for example, from about 30 minutes to about 12 hours longer i.e. 24 or 48 hours. It should be understood that optimal soak times can vary with facilities and production scale. The extraction solvent is then filtered off the biomass and retained for further processing. Multiple organic solvent extractions or a continuous flow extraction system may optionally be used to effect greater efficiency in extracting taxanes from the biomass. The eluate can be monitored to determine an optimum end point for the extraction(s), including monitoring the color of the eluate, spectrographic analysis, and chromatographic techniques. The volume of extraction solvent and length of soak time used for any one-batch extraction, or the solvent flow rate in a continuous flow system may be adjusted to optimize yields. Though not required, techniques such as agitation, sonication, heating ($\leq$ about 40° C.), application of back pressure or vacuum to filter off the extract, and pressing the biomass to facilitate removal of extract from residual biomass may all be used to advantage in improving extraction efficiency. Factors such as solvent volumes, soak times or continuous flow rates and the use of the listed techniques, with time constraints and the equipment and process costs involved, can be optimized to increase the yield of taxanes extracted from a given biomass and to suit the particular needs of a given production facility.

In one preferred embodiment, the filtrate fractions containing solubilized taxanes are pooled and the solvent is removed by conventional means. Any means of solvent removal or exchange known in the art is contemplated provided the product does not contain residual solvents that would interfere with downstream processing of the extract. One preferred method includes evaporation under reduced pressure with recovery of the solvent. The resulting substantially solvent-free extract is further processed to recover individual taxanes from the extract.

It has been surprisingly found that an enriched fraction of taxanes may be obtained from an organic solvent extract as described above without an initial fractionation procedure, such as, liquid:liquid partitioning of the crude organic extract, prior to chromatographic separation as required by prior art taxane purification methods.

The term fractionation as used in this invention includes the separation or partial separation of impurities and/or one or more taxanes and includes liquid:liquid partitioning, and the like, but not filtration to remove solid particles or redissolution of a solid material.

The present invention greatly enriches the taxane content of the crude extract by a selective adsorption and desorption using an adsorption resin. The extract is adsorbed onto the adsorption resin in a solvent that induces the taxanes to adsorb onto the resin. The resin is then washed with a wash solvent that elutes at least a portion of the impurities while retaining the taxanes on the resin. The resin is next eluted with an elution solvent that induces desorption of the taxanes while retaining a second part of the impurities on the resin. The resulting taxane enriched eluate may then be used as a taxane concentrate or forward processed to further purify individual taxane compounds.

FIG. 1 is a diagram of one preferred embodiment. One or more taxanes are separated from the crude extract and other impurities by adsorption on a silica resin and taking advantage of differences in the polarity of taxanes and impurities in the extract. The extract as described above is adsorbed onto a silica resin followed by selective elutions with a series of increasingly polar solvent mixtures. Preferably, the increasingly polar solvent mixtures are also increasingly hydrophilic. The silica resins useful in the present invention are commercially available. Inexpensive silica gel can be used, provided it will adsorb desirable taxanes and retain highly polar molecules.

In one preferred embodiment, an initial amount of silica resin is mixed with concentrated extract and then the extraction solvent is removed to provide a powder. Typical ratios of resin to extract are between about 4:1 and 1:2 by weight. The resulting resin/extract mixture is placed on a column comprising a second portion of resin. Typically the ratio of column resin to resin/extract mixture is between about 1:2 and about 10:1 by weight. The loading ratio of total resin to extract is typically between about 2:1 and about 10:1. Larger ratios may be used if desired.

In an alternative embodiment, the extract may be dissolved in the adsorption solvent and mixed with the resin or passed over a column of the resin to adsorb the extract onto the resin. Again, the loading ratio of total resin is typically between about 2:1 and about 10:1. Ratios greater than 10:1 can also be used.

After the extract has been adsorbed onto the resin, the resin is washed with a wash solvent to elute non-polar impurities from the silica resin while retaining taxanes and polar impurities on the resin. The wash solvent is a non-polar solvent mixture that maintains the adsorption of taxanes on the resin, but elutes non-polar impurities such as waxes, fats and lipids. The column is next eluted with an elution solvent that is miscible with the wash solvent, but is more polar than the wash solvent. The elution solvent induces the desorption of taxanes from the resin, while retaining impurities that are more polar than the taxanes on the resin. This results in an eluate that is significantly enriched in one or more taxanes and essentially free of extracted impurities that are distinguishably more or less polar than the taxanes.

In one preferred embodiment, the silica resin is eluted in multiple steps with solvent mixtures of increasing polarity to effect at least a partial separation of individual taxanes from the resin. For example, a taxol/cephalomannine pool may beneficially be at least partially separated from the more polar 10-deacetylated taxane derivatives.

In another embodiment, a continuous flow moble phase containing an elution gradient of increasing polarity is used to develop the chromatography column and elute one or more taxanes from the resin. The fractions containing the desired taxane(s) are collected and pooled.

Preferred adsorption, wash and elution solvent mixtures are mixtures of one or more non-polar organic solvents with one or more miscible polar organic solvents. A series of solvent mixtures of increasing polarity is obtained by increasing the ratio of polar to non-polar solvents. Preferred non-polar solvents include, for example, $C_5$–$C_8$ alkanes and toluene. Preferred polar solvents include, for example, $C_1$–$C_6$ alcohols, $C_1$–$C_4$ alkyl ketones, $C_1$–$C_5$ alkyl esters of $C_1$–$C_5$ carboxylic acids, $C_1$–$C_4$ carboxylic acids, $C_1$–$C_4$ alkyl nitriles, $C_4$–$C_8$ alkyl ethers, chloroform, dichloromethane, nitromethane, and mixtures thereof. Exact ratios are optimized for the desired separation of components depending on the specific combination of resin, its activity, the selection of solvents used, the taxanes desired and the biomass source. This optimization can be accomplished, for example, by test separations of mixtures of purified compounds or in pilot scale separations.

Other adsorption media, such as alumina, CELITE®, FLORSIL®, and SEPHADEX®, can be envisioned that would likewise allow an initial enrichment of the yew biomass extract without the need for a liquid:liquid partitioning step. Such adsorption media may include resins that separate compounds on the basis of chemical characteristics other than degree of polarity, or by specific biorecognition, and are within the scope of the present invention.

The taxane enriched eluate may be used as a crude taxane concentrate, or may be further processed to isolate individual taxanes. The elution solvent may be removed, as for example by evaporation under reduced pressure or other means common in the art to obtain a substance concentrated in taxanes and having a gum consistency.

In another embodiment of the present invention, it has been found that individual taxanes can be purified to better than 90%, and optionally to better than 98% purity in a single chromatographic step from the taxane enriched eluate of the above silica adsorption step using non-silica based, non-ionic, hydrophobic-interaction macropolymer resins. The desolvated taxane containing fractions from the above described silica adsorption enrichment are reconstituted in a suitable water miscible organic solvent or aqueous mixture thereof. Preferred organic solvents include, for example, straight chain, branched and cyclic: $C_1$–$C_6$ alcohols, $C_3$–$C_7$ alkyl ketones, $C_1$–$C_5$ alkyl esters of $C_1$–$C_5$ carboxylic acids, $C_1$–$C_4$ carboxylic acids, $C_1$–$C_4$ alkyl nitriles, $C_4$–$C_8$ alkyl ethers, and mixtures thereof. The aqueous content of the reconstitution solvent is limited by the solubility of the desolvated taxane containing fractions.

The hydrophobic-interaction resins useful in the present invention are non-silica based macroporous hydrophobic macropolymers that separate molecules based on hydrophobic-interactions and size exclusion interactions with the resin. Further advantages of the polymer resins useful in the present invention are that they are reusable and that they avoid the high cost of typical high-grade reverse phase silica-based resins. Resins comprising polymers and copolymers based on polyaromatic, polyacrylate, polymethacrylate, polystyrene and modified polystyrene, particularly brominated polystyrene, have been used to advantage. A variety of non-ionic, hydrophobic-interaction resins are commercially available.

Particularly suitable non-ionic, hydrophobic-interaction resins will have a particle size range of from about 5 $\mu$m to about 500 $\mu$m, preferably with an average particle size of between about 5 $\mu$m and about 250 $\mu$m, and pore diameters ranging from about 5 Å to about 500 Å, preferably from about 10 Å to about 400 Å. In another preferred embodiment, the average pore size will be less than about 300 Å; still more preferably the average pore size will be less than about 150 Å. The resin will have an average BET surface area of greater than about 30 $m^2/g$.

Suitable non-ionic, hydrophobic-interaction resins can be produced as described in U.S. Pat. No. 3,418,262, incorporated herein by reference. By way of example, but without limitation, a suitable resin can be produced by the aqueous suspension copolymerization of styrene and divinyl benzene at about 80–90° C. in the presence of organic diluents having good compatibility with the styrene monomer, but low miscibility with water, such as n-hexane, toluene, or ethylene glycol monoethyl ether. Saturated carboxylic acids, such as those mentioned in U.S. Pat. No. 3,418,262, may also be added in various proportions to tailor the resin particle architecture as desired.

The hydrophobic-interaction resin is equilibrated with a loading solvent or initial wash solvent comprising an aqueous:organic solvent mixture that induces the adsorption of taxanes on the resin, but allows the flow-through of impurities that are more hydrophilic than the taxanes. Most of the hydrophilic impurities such as pigments, salts, sugars and water soluble proteins not already removed in the silica adsorption step above are thereby eluted from the resin by the loading or wash solvent. Taxanes are then eluted from the column with an elution solvent comprising a buffered or unbuffered aqueous:organic solvent mixture that has a higher organic solvent content than the adsorption solvent, so as to selectively induce desorption of desired taxanes while retaining impurities more hydrophobic than the taxanes on the resin. Hydrophobic impurities such as waxes, lipids and fats not removed by the silica adsorption step above are retained on the resin. Collected fractions of eluate contain individual taxanes at better than 90% purity and optionally at better than 98% purity. A suitable hydrophobic-interaction resin/loading (wash) solvent/elution solvent combination can be optimized to provide elution profile conditions to isolate particular taxanes as desired. Conditions may be optimized by test separations on mixtures of previously purified taxanes with a given resin/solvent system combination. The test separations can entail use of TLC, HPLC techniques and the like to optimize separation conditions.

In another embodiment, a continuous flow elution gradient with a gradually increasing ratio of organic solvent-to-water for the elution solvent may be used to elute one or more taxanes from the resin with the appropriate collection and pooling of taxane(s) containing fractions.

In an alternative preferred embodiment, shown diagrammatically as optional in FIG. 1, the ground biomass is initially extracted with aqueous extraction solvent with or without buffering to remove water soluble impurities, such as, water soluble proteins, salts, sugars, and pigments, before extracting taxanes with the organic extraction solvent. It is desireable to not include organic solvents in the aqueous extraction solution to prevent leaching of taxanes into the aqueous extract. For example, it is known that as little as 10% methanol in the aqueous extraction buffer will result in unacceptable leaching of taxanes. Preferably the aqueous extraction solvent should include less than about 10%, by weight, organic solvent(s); more preferably, less than about 5%, by weight, organic solvent(s).

Multiple batch mode aqueous extractions or a continuous flow extraction system may optionally be used to effect greater efficiency in removal of water soluble impurities. Many methods for monitoring the eluate can be used to determine an optimum end point, including monitoring the color of the eluate. The volume of aqueous extraction buffer and length of soak time used for any one batch extraction, or the solvent flow rate in a continuous flow system are not critical. Optimal conditions will vary with the starting material, batch size, and equipment used.

Techniques such as agitation, sonication, heating ($\leq$about 40° C. to avoid degradation or epimerization of the taxanes), application of back pressure or vacuum to filter off the extract, and pressing the biomass to facilitate removal of aqueous extract from residual biomass may all optionally be used to advantage to improve extraction efficiency. Factors such as solvent volumes, soak times or continuous flow rates and the use of the listed techniques, with time constraints and the equipment and process costs involved, can be optimized to maximize the yield of taxanes extracted from a given biomass and to suit the particular needs of a given production facility. After removal of the aqueous filtrate, the residual biomass is ready for organic solvent extraction as described above.

Figure 2:
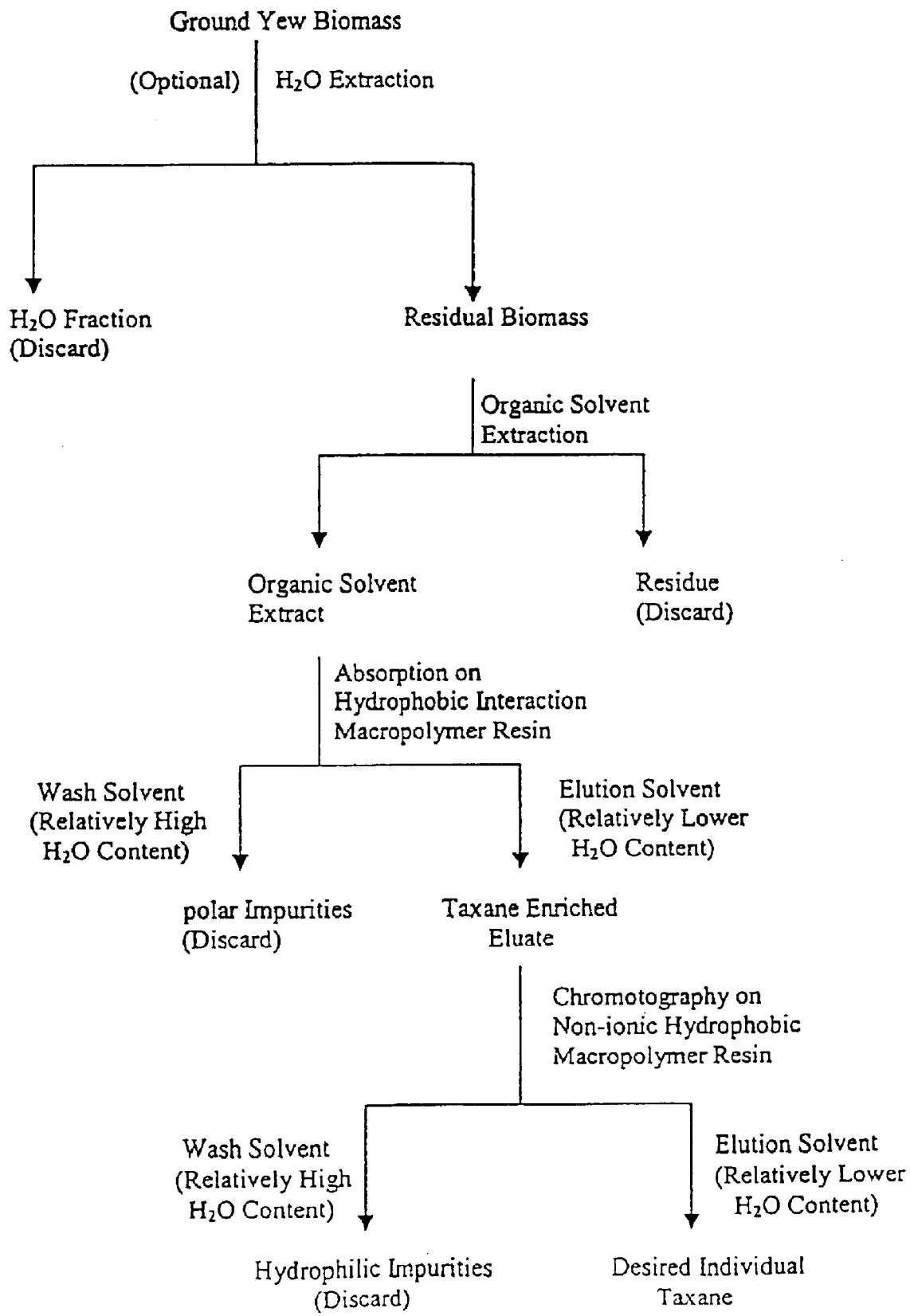
FIG. 2 is process flow diagram illustrating an alternative scheme for the isolation of taxanes from yew biomass according to this invention.

In an alternative embodiment of the present invention illustrated diagrammatically in FIG. 2, the silica resin adsorption step is replaced with adsorption on a non-ionic hydrophobic-interaction macropolymer resin, followed by sequential selective elutions with a series of buffered or unbuffered aqueous solvent mixtures having increasing ratios of organic solvent to buffered or unbuffered water. As with the silica adsorption step, this hydrophobic-interaction resin adsorption step results in an eluate significantly enriched in taxanes. Resins suitable for the hydrophobic-interaction adsorption step are the same as or related to those described for the hydrophobic-interaction chromatography step above, though a lesser grade of selectivity may be used at this early stage in the process without a reduction in yield or purity of the final product.

The hydrophobic-interaction resin is equilibrated with a buffered or unbuffered aqueous organic adsorption solvent low enough in organic solvent content to induce adsorption of taxanes into the resin. The extract is then dissolved in the adsorption solvent and mixed with the equilibrated resin or passed over a column of the equilibrated resin to adsorb the extract into the resin. The hydrophobic-interaction resin is then washed with a wash solvent comprising a buffered or unbuffered aqueous organic solvent mixture that retains the taxanes adsorbed on the resin, but allows impurities more hydrophilic than the taxanes, such as water soluble proteins and peptides, salts, sugars, and pigments to wash from the resin. The column is next eluted with an elution solvent comprising a buffered or unbuffered aqueous:organic solvent mixture that has a higher ratio of organic solvent to water than the wash solvent, that is to say, more hydrophobic, to induce the desorption of taxanes from the resin while retaining impurities more hydrophobic than the taxanes on the resin. The hydrophobic resin may then be alternatively cleaned for reuse by elution with an organic solvent that desorbs any remaining compounds from the resin.

In one preferred embodiment, the resin is eluted in multiple steps with solvent mixtures of increasing organic solvent to water ratio to effect at least a partial separation of individual taxanes from the hydrophobic resin. For example, a taxol/cephalomannine pool may be effectively separated from the more hydrophilic 10-deacetylated taxane derivatives.

In another embodiment, a continuous flow elution gradient of increasing organic solvent to water ratio may be used to elute taxanes from the resin with the collection and pooling of appropriate taxane containing fractions.

The specific elution solvents used will depend on the selection of the hydrophobic-interaction resin used and the specific taxanes desired as end products. Buffered or unbuffered water miscible organic solvent may be used. Preferred organic solvents for use in the buffered or unbuffered aqueous:organic solvent mixtures include $C_1$–$C_6$ alkyl alcohols, $C_3$–$C_7$ alkyl ketones, $C_1$–$C_5$ alkyl esters of $C_1$–$C_5$ carboxylic acids, $C_1$–$C_4$ carboxylic acids, $C_1$–$C_4$ alkyl nitriles, $C_4$–$C_8$ alkyl ethers and mixtures thereof.

In one preferred embodiment of the present invention, taxane-containing fractions eluted from the hydrophobic-interaction resin are pooled, and the solvent is removed by any art-recognized means. Preferred means include vacuum evaporation with recovery of the solvents for recycling. This taxane-enriched mixture may be reconstituted in an appropriate solvent for downstream purification, such as by chromatography on a second hydrophobic-interaction resin as described above.

In one preferred embodiment, the eluate from the organic solvent extraction of the biomass is directly passed over the equilibrated hydrophobic-interaction resin without first removing the extraction solvent. The solvent can be diluted with buffered or unbuffered water to facilitate and enhance the adsorption of taxanes onto the resin. This embodiment eliminates a solvent removal step as well as the need to handle an intermediate mixture. The more polar impurities such as water soluble impurities elute from the hydrophobic-interaction resin preferentially over the desired taxanes. This effectively separates these polar impurities from the desired taxanes. Consequently the initial aqueous extraction of the plant biomass prior to the organic solvent extraction described above often can be eliminated without decreasing the purity of the isolated taxanes. This provides added advantages of increasing yield, while also decreasing processing time, energy and costs.

While the invention has been described in detail in the foregoing description, the same is to be considered as illustrative and not restrictive in character, it being understood that only the preferred embodiments have been shown and described. The invention will now be further described with reference to the following specific Example. It will be understood that this Example is also only illustrative and is intended only to provide further understanding of the methods and process of the present invention.

EXAMPLE

Dried needles from *T. media* "Hicksii" (500 g) were ground and rehydrated in conjunction with an aqueous extraction by soaking the biomass in 2.7L water for about 1 hr. The aqueous fraction was filtered off the residual biomass with vacuum. The aqueous extract was determined to be substantially free of taxanes by analytical chromatography (result not shown).

Figure 3:
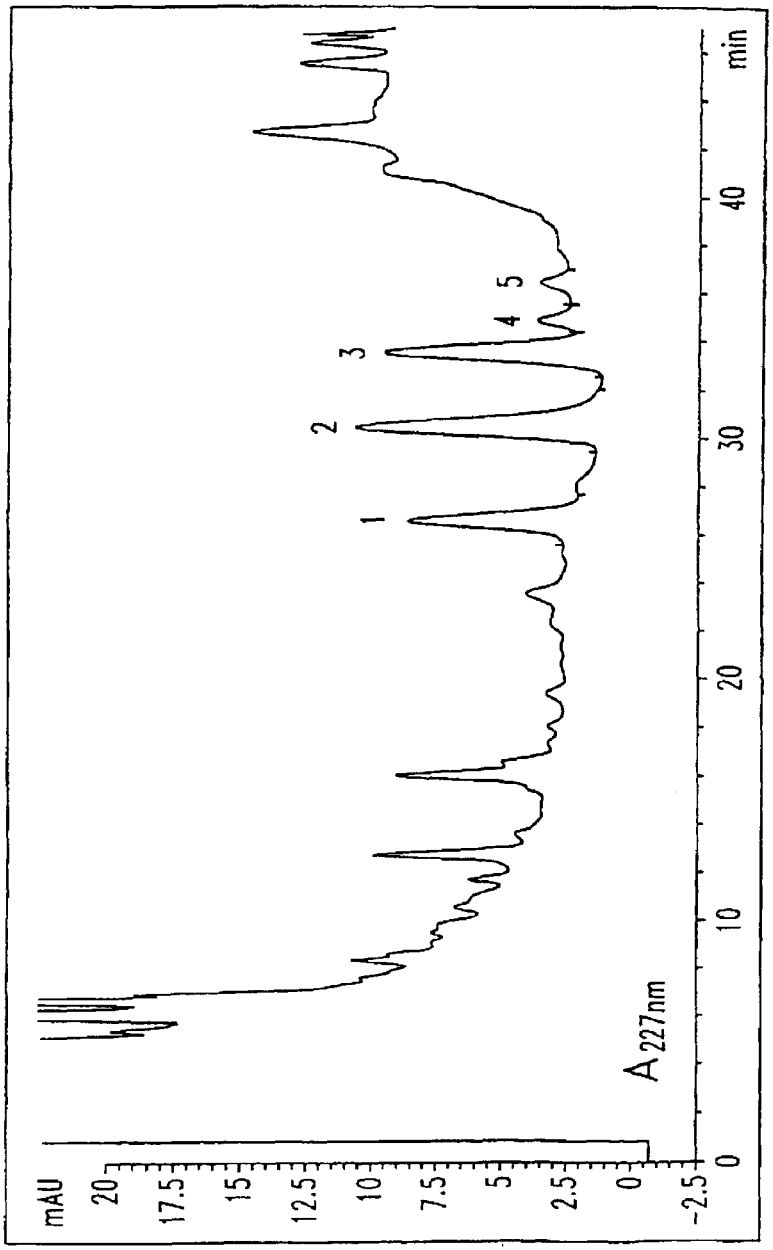
FIG. 3 is a chromatogram of a methanol extract of yew needles.

The residual biomass was then extracted with 3.5 L methanol at room temperature. The eluate was collected and dried by vacuum evaporation to yield 37.5 g of a gummy solid. The methanol extract was analyzed chromatographically (see FIG. 3).

Figure 4:
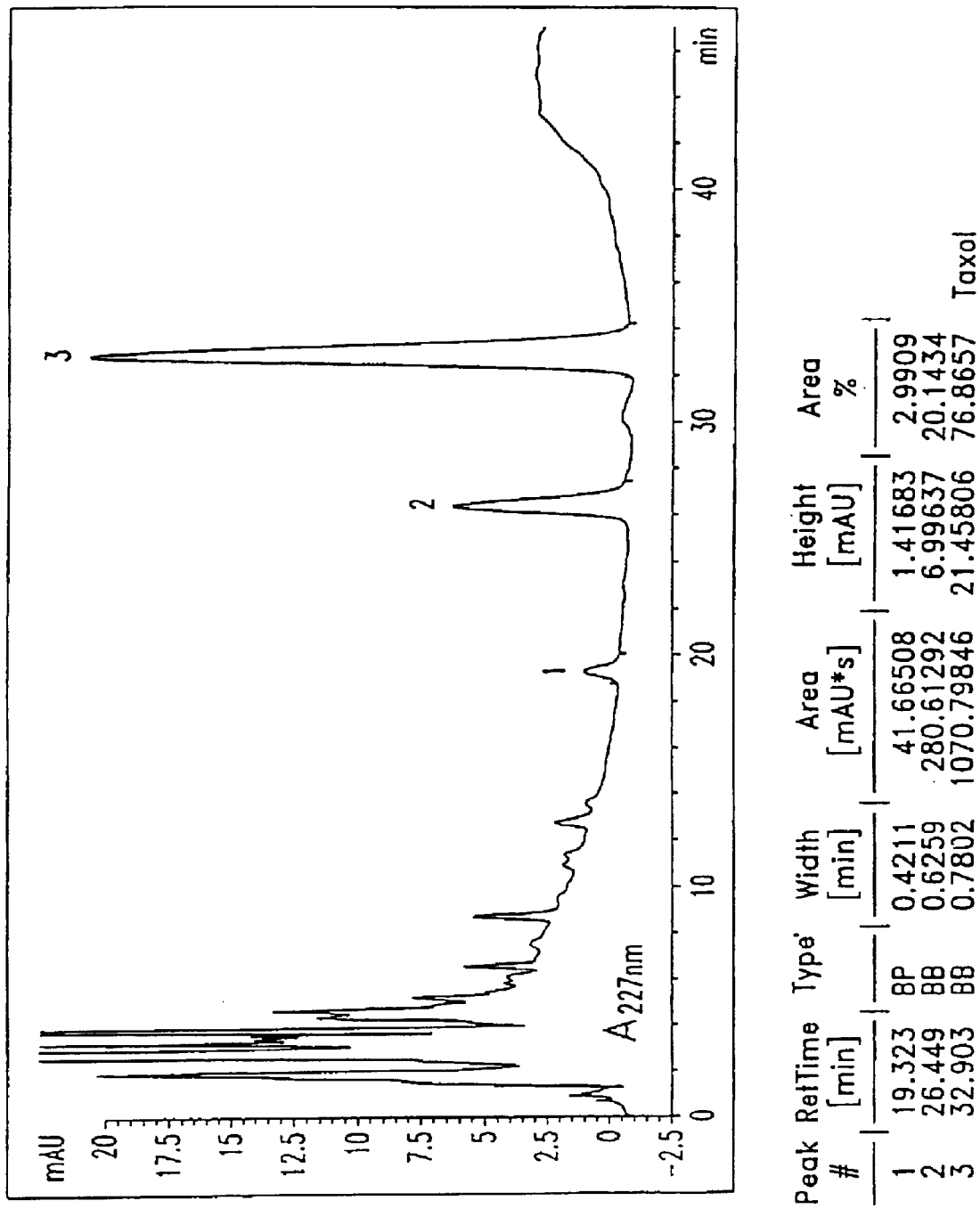
FIG. 4 is a chromatogram of a methanol extract from yew needles enriched in taxanes by selective absorption onto and elution from a silica resin.

The methanol extract was reconstituted in hexane:acetone solvent (20:3 by volume) and filtered through 150 g silica resin to absorb the taxanes to the silica. The silica was eluted sequentially with 5 L 20:3 hexane:acetone, 4.5 L 20:6 hexane:acetone, 2.5 L 20:9 hexane:acetone. The first 1.5 liters of the 20:9 hexane:acetone eluate was enriched in taxol/cephalomannine as determined chromatographically (see FIG. 4). The solvent was removed by vacuum evaporation to yield 1.01 g of a gummy solid.

Figure 5:
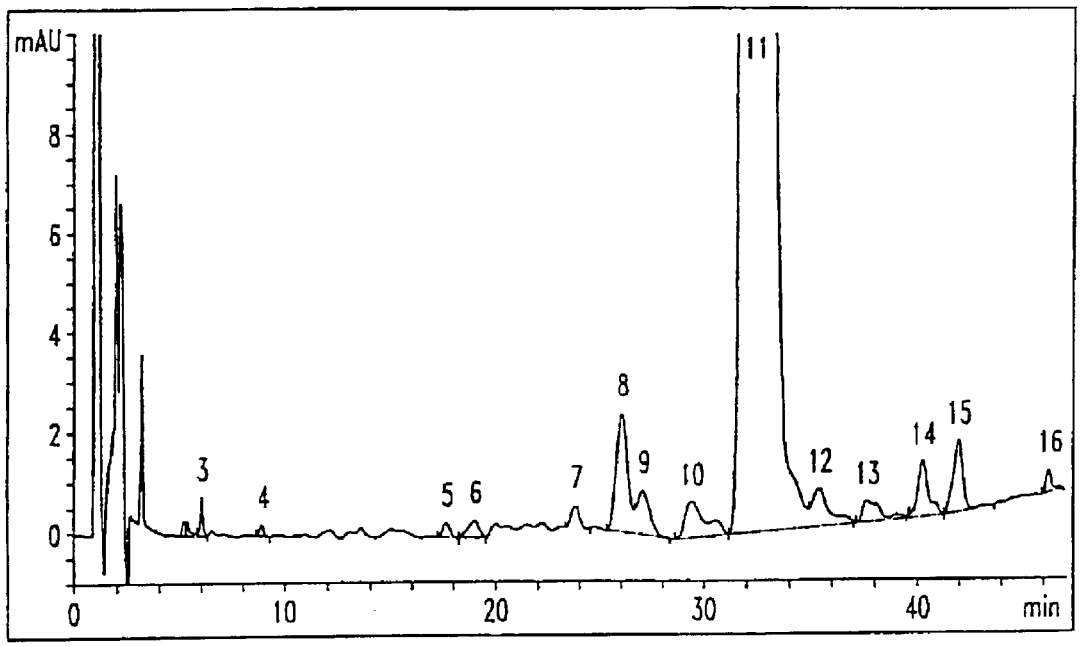
FIG. 5 is a chromatogram of the taxane enriched material analyzed in FIG. 3, further enriched in taxol by chromatography on a non-ionic, hydrophobic-interaction macropolymer resin.

The taxol/cephalomannine enriched solid was reconstituted in 2.0 mL ethanol and chromatographed on a styrene/divinyl benzene copolymer non-ionic, hydrophobic-interaction polyaromatic resin with an average particle size of 5–120 μm, average pore size of about 150 Å and an average BET surface area of greater than 30 $m^2/g$. The sample was loaded onto the column and eluted with 40% (by volume) isopropanol in water. Fractions containing cephalomannine, taxol and a mixture of 7-epi-taxol and 10-deacetyltaxol were collected. The taxol fraction was analyzed chromatographically (see FIG. 5).

Figure 6:
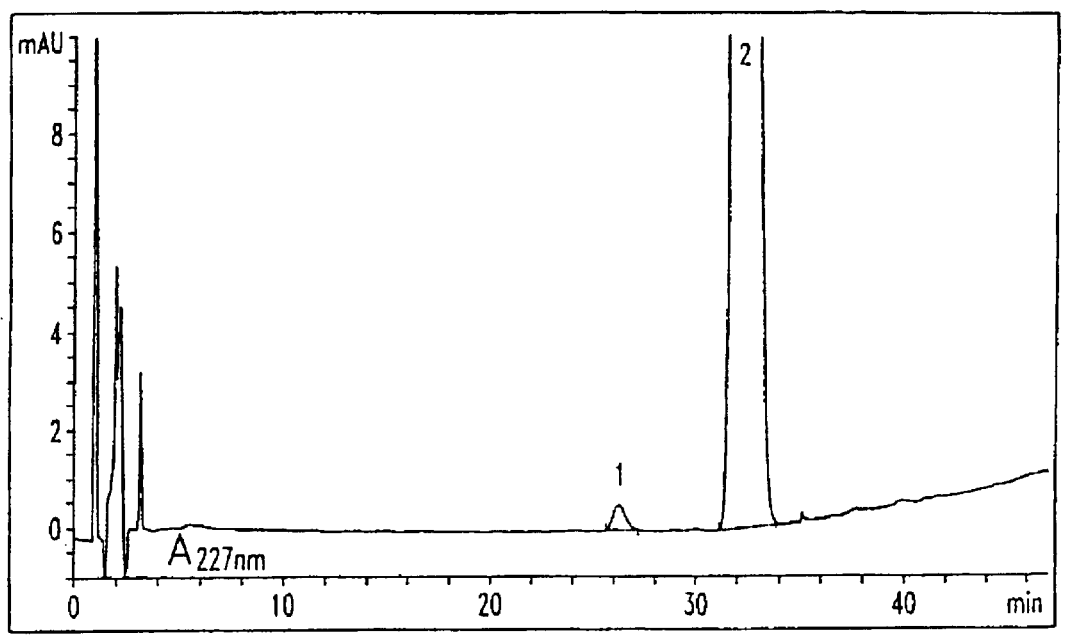
FIG. 6 is a chromatogram of the taxol-enriched material analyzed in FIG. 4, further purified by crystallization.

The taxol containing fraction was further purfied by crystallization from a hexane/acetone solution to yield 65 mg of 99.8% pure taxol as determined chromatographically (see FIG. 6).

While the invention has been illustrated and described in detail in the figures and foregoing description and example, this is to be considered illustrative and not restrictive. All modifications and equivalents of the elements of the disclosed invention that come within the spirit of the invention as defined by the following claims are contemplated and their protection is desired.

We claim:

1. A process for purifying taxanes obtained from a plant biomass containing taxanes, the process comprising:
    extracting the biomass with an organic extraction solvent able to dissolve taxanes, forming an extract;
    absorbing the extract onto an absorbent medium;
    eluting the absorbent medium with a first elution solvent to obtain an eluent enriched in desired taxanes;
    eluting the eluent through a non-ionic, hydrophobic-interaction resin with a second elution solvent to provide at least two taxane compounds.

2. The process of claim 1, wherein the organic extraction solvent is methanol.

3. The process of claim 1, wherein the absorbent medium is silica.

4. The process of claim 1, wherein the first elution solvent is a mixture of hexane and acetone.

5. The process of claim 4, wherein the first elution solvent mixture has increasing hydrophilicity as it elutes the absorbent medium.

6. The process of claim 2, wherein the second elution solvent is a mixture of isopropanol in water.

7. The process of claim 1, wherein the non-ionic, hydrophobic-interaction resin is a macropolymer selected from the group consisting of: polyaromatic, polyacrylate, polymethacrylate, polystyrene, brominated polystyrene and mixtures thereof.

8. The process of claim 1, wherein the taxanes are one or more taxanes selected from the group consisting of: taxol, cephalomannine, baccatin III, 10-deacetyltaxol, 10-deacetylcephalomannine, 10-deacetylbaccatin III, 7-xylosyltaxol, 7-xylosylcephalonammine, 7-xylosylbaccatin III, and related analogs.

9. The process of claim 1, wherein the biomass is derived from yew needles, stems, roots, plant cells in culture or a mixture thereof.

10. The process of claim 1, further comprising recovering one or more individual taxane compounds in at least 90% pure form by chromatography on a second adsorption medium.

11. A process for purifying taxanes obtained from a plant biomass containing taxanes, the process comprising:
    extracting the biomass with an organic extraction solvent able to dissolve taxanes, forming an extract;
    absorbing the extract onto an absorbent medium;
    eluting the absorbent medium with sequentially more polar solvents to obtain an eluent enriched in desired taxanes;
    removing the solvent from the taxane enriched eluent to generate a taxane enriched solid;
    dissolving the taxane enriched solid to obtain a taxane enriched solution containing the same number of taxane compounds as the taxane enriched solid;
    eluting the taxane enriched solution through a non-ionic, hydrophobic-interaction resin to provide at least two taxane compounds.

12. The process of claim 11, wherein the organic extraction solvent is methanol.

13. The process of claim 11, wherein the absorbent medium is silica.

14. The process of claim 11, wherein the non-ionic, hydrophobic-interaction resin is a macropolymer selected from the group consisting of polyaromatic, polyacrylate, polymethacrylate, polystyrene, brominated polystyrene and mixtures thereof.

15. The process of claim 11, wherein the taxanes are one or more taxanes selected from the group consisting of: taxol, cephalomannine, baccatin III, 10-deacetyltaxol, 10-deacetylcephalomannine, 10-deacetylbaccatin III, 7-xylosyltaxol, 7-xylosylcephalonammine, 7-xylosylbaccatin III, and related analogs.

16. The process of claim 11, wherein the biomass is derived from yew needles, stems, roots, plant cells in culture or a mixture thereof.

17. The process of claim 11, further comprising recovering one or more individual taxane compounds in at least 90% pure form by chromatography on a second adsorption medium.

18. A process for the isolation of desired taxanes from a plant biomass containing taxanes, the process comprising:
   extracting the biomass with an aqueous solvent, forming a pre-extracted biomass;
   extracting the pre-extracted biomass with an organic extraction solvent able to dissolve taxanes, forming an extract;
   absorbing the extract onto an absorbent medium;
   washing the absorbent medium with a wash mixture to elute impurities more hydrophilic than the desired taxanes while retaining the desired taxanes on the absorbent medium;
   eluting the desired taxanes from the absorbent medium with an elution mixture that is more hydrophobic than the wash mixture and that induces desorption of the desired taxanes from the absorbent medium while retaining impurities more hydrophobic than the desired taxanes, absorbed on the absorbent medium to obtain an eluent enriched in desired taxanes;
   removing the solvent from the eluent enriched in desired taxanes to obtain a taxane-enriched solid;
   dissolving the taxane-enriched solid in a solvent to generate a taxane enriched composition having the same number of taxanes as the eluent enriched in desired taxanes;
   eluting the taxane enriched composition through a non-ionic, hydrophobic-interaction resin to provide at least two desired taxane compounds.

19. The process of claim 18, wherein the organic extraction solvent is methanol.

20. The process of claim 18, wherein the absorbent medium is silica.

21. The process of claim 18, wherein the non-ionic, hydrophobic-interaction resin is a macropolymer selected from the group consisting of polyaromatic, polyacrylate, polymethacrylate, polystyrene, brominated polystyrene and mixtures thereof.

22. The process of claim 18, wherein the taxanes are one or more taxanes selected from the group consisting of: taxol, cephalomannine, baccatin III, 10-deacetyltaxol, 10-deacetylcephalomannine, 10-deacetylbaccatin III, 7-xylosyltaxol, 7-xylosylcephalonammine, 7-xylosylbaccatin III, and related analogs.

23. The process of claim 18, wherein the biomass is derived from yew needles, stems, roots, plant cells in culture or a mixture thereof.

24. The process of claim 18, further comprising recovering one or more individual taxane compounds in at least 90% pure form by chromatography on a second adsorption medium.

25. A process for the isolation of taxanes from a plant biomass, said process comprising:
   extracting the biomass with an organic extraction solvent able to dissolve taxanes to obtain an extract containing desired taxanes and hydrophilic and hydrophobic impurities;
   adsorbing said extract onto a first, hydrophobic interaction macropolymer resin with a polar, buffered or unbuffered aqueous:organic solvent adsorption mixture that induces the absorption of desired taxanes onto said first hydrophobic-interaction resin;
   washing said first hydrophobic-interaction resin with a buffered or unbuffered aqueous:organic solvent wash mixture to elute impurities more hydrophilic than the desired taxanes from said first hydrophobic-interaction resin while retaining desired taxanes adsorbed on said first hydrophobic-interaction resin; and
   eluting desired taxanes from said first hydrophobic-interaction resin with a buffered or unbuffered aqueous:organic solvent elution mixture that is more hydrophobic than said wash mixture and that induces desorption of desired taxanes from said first hydrophobic-interaction resin while retaining impurities more hydrophobic than the desired taxanes, adsorbed on said first hydrophobic-interaction resin to obtain an eluate enriched in desired taxanes.

26. The process of claim 54 wherein the extraction solvent contains from 0% to about 50% by volume buffered or unbuffered water and one or more solvents selected from the group consisting of $C_1$–$C_6$ alkyl alcohols, $C_3$–$C_7$ alkyl ketones, $C_1$–$C_5$ alkyl esters of $C_1$–$C_5$ carboxylic acids, $C_1$–$C_4$ carboxylic acids, $C_1$–$C_4$ alkyl nitriles, $C_4$–$C_8$ alkyl ethers, chloroform, dichloromethane, nitromethane, toluene and mixtures thereof.

27. The process of claim 54 wherein the organic solvents in the buffered or unbuffered aqueous:organic solvent adsorption, wash and elution mixtures are one or more solvents selected from the group consisting of $C_1$–$C_6$ alkyl alcohols, $C_3$–$C_7$ alkyl ketones, $C_1$–$C_5$ alkyl esters of $C_1$–$C_5$ carboxylic acids, $C_1$–$C_4$ carboxylic acids, $C_1$–$C_4$ alkyl nitriles, $C_4$–$C_8$ alkyl ethers, and mixtures thereof.

28. The process of claim 54 further comprising recovering one or more individual taxanes in at least 90% pure form from the taxane-enriched eluate by chromatography on a second hydrophobic-interaction macropolymer resin.

29. The process of claim 57 wherein the first and second hydrophobic-interaction macropolymer resins independently of one another are a macropolymer or copolymer derived from one or more polymers selected from the group consisting of polyaromatic, polyacrylate, polymethacrylate, polystyrene, modified polystyrene and mixtures thereof.

30. The process of claim 58 wherein each resin independently has a particle size range of between about 5 $\mu$m and about 500 $\mu$m, and a pore size range of between about 5 Å and about 500 Å.

31. The process of claim 59 wherein each resin independently has an average particle size of between about 5 $\mu$m and about 250 $\mu$m, and a pore size range of between about 10 Å and about 400 Å.

32. The process of claim 58 wherein at least one of the first and second hydrophobic-interaction macropolymer resins is a copolymer of styrene and divinylbenzene produced by suspension copolymerization in water and a water immiscible organic solvent.

33. The process of claim 61 wherein at least one of the first and second hydrophobic-interaction resins has an average particle size of between about 5 $\mu$m and about 250 $\mu$m, an average pore size less than about 300 Å, and an average BET surface area greater than about 30 m²/g.

34. The process of claim 54 comprising extracting the biomass with an aqueous extraction solvent containing no more than 10% organic solvents prior to extracting the biomass with an organic extraction solvent, wherein said aqueous extraction solvent is selected to minimize leaching of taxanes from the biomass during said extraction.

35. The process of claim 63 wherein the biomass is ground in the aqueous extraction solvent.

* * * * *

UNITED STATES PATENT AND TRADEMARK OFFICE
CERTIFICATE OF CORRECTION

PATENT NO. : 6,939,978 B2 Page 1 of 1
DATED : September 6, 2005
INVENTOR(S) : Chang et al.

It is certified that error appears in the above-identified patent and that said Letters Patent is hereby corrected as shown below:

<u>Title page,</u>
Item [75], Inventors, for "Ching-jer Chang", replace "Lafayette" with -- West Lafayette --; and for "Xiao-jie Tong", replace "Palisades Park" with -- Warren --.

<u>Column 12,</u>
Line 14, replace "eluent" with -- eluent enriched in desired taxanes --.
Line 39, delete ", and related analogs".

<u>Column 13,</u>
Lines 11 and 60, delete ", and related analogs".

<u>Column 14,</u>
Lines 27, 35 and 42, replace "54" with -- 25 --.
Line 46, replace "57" with -- 28 --.
Lines 52 and 60, replace "58" with -- 29 --.
Line 56, replace "59" with -- 30 --.
Line 65, replace "61" with -- 32 --.

<u>Column 15,</u>
Line 3, replace "54" with -- 25 --.

<u>Column 16,</u>
Line 3, replace "63" with -- 34 --.

Signed and Sealed this

Second Day of May, 2006

JON W. DUDAS
*Director of the United States Patent and Trademark Office*